US006652590B1

United States Patent
Zitnansky et al.

(10) Patent No.: US 6,652,590 B1
(45) Date of Patent: Nov. 25, 2003

(54) CEMENTLESS TOTAL REPLACEMENT OF THE HUMAN HIP JOINT

(76) Inventors: Marcel Zitnansky, Racianska 63, 831 02 Bratislava (SK); Lubos Rehak, Bajzova 14, 821 08 Bratislava (SK); Frantisek Makai, Zrinskeho 7, 811 03 Bratislava (SK)

( * ) Notice: Subject to any disclaimer, the term of this patent is extended or adjusted under 35 U.S.C. 154(b) by 0 days.

(21) Appl. No.: 10/018,097
(22) PCT Filed: May 11, 2000
(86) PCT No.: PCT/SK00/00007

§ 371 (c)(1),
(2), (4) Date: Nov. 13, 2001

(87) PCT Pub. No.: WO00/69371

PCT Pub. Date: Nov. 23, 2000

(30) Foreign Application Priority Data

May 13, 2000 (SK) .............................. 0635-99

(51) Int. Cl.⁷ .................................. A61F 2/32
(52) U.S. Cl. .................... 623/22.15; 623/22.15
(58) Field of Search ............ 623/22.15, 22.11, 623/22.21, 22.4, 23.11, 23.15, 22.32, 22.23, 22.38, 23.14, 23.24, 23.26, 23.29, 23.31, 23.35, 23.36, 23.4, 22.27, 22.31; 433/173

(56) References Cited

U.S. PATENT DOCUMENTS

| | | | | |
|---|---|---|---|---|
| 5,002,581 A | * | 3/1991 | Paxson et al. | 623/23 |
| 5,370,694 A | * | 12/1994 | Davidson | 623/16 |
| 5,391,422 A | * | 2/1995 | Omori et al. | 428/212 |
| 5,443,520 A | | 8/1995 | Zweymuler et al. | |
| 5,514,184 A | * | 5/1996 | Doi et al. | 623/23 |
| 5,645,601 A | | 7/1997 | Pope et al. | |
| 5,702,473 A | * | 12/1997 | Albrektsson et al. | 623/22 |
| 5,728,161 A | * | 3/1998 | Camino et al. | 623/19 |
| 5,879,407 A | * | 3/1999 | Waggener | 623/22 |

FOREIGN PATENT DOCUMENTS

| | | |
|---|---|---|
| FR | 2598609 | 11/1987 |
| GB | 2029229 | 3/1980 |

* cited by examiner

Primary Examiner—Eduardo C. Robert
Assistant Examiner—David C Comstock
(74) Attorney, Agent, or Firm—Hovey Williams LLP

(57) ABSTRACT

The solution is based on the fact, that on the surface of the acetabulum (3) there is a self-drilling thread, containing at least three independent teeth (41, 42 and 43) which advantageously have a concave shape of the cutting edge and a truncated pike, whereas the planes of their upper edges lie on a spherical surface. The femoral component (1) has on outer side of its lower part (11) an asymmetric tapering under the angle $\gamma=20°$ to $70°$ and on the upper part (13) a convexly widened outer side. Minimally on the lower part (11) and middle part (12) of the inner side of the femoral component (1) at least one longitudinal groove (5) is provided, and minimally on one side plane of the middle part (12) and/or of the upper part (13) there, is provided at least one transversal rib (6), forming with the axis of the wedge an angle $\beta=70°$ to $110°$. At least on a part of the outer surface of the acetabulum (3) a nanocrystalline diamond or hydroxyapatite layer is preferably created and at least on a part of the outer surface of the femoral component (1) a nanocrystalline diamond and/or hydroxyapatite layer is provided.

20 Claims, 8 Drawing Sheets

CEMENTLESS TOTAL REPLACEMENT OF THE HUMAN HIP JOINT

BACKGROUND OF THE INVENTION

The invention concerns cementless total hip replacement prostheses (further THR) as replacement of the human hip joint applied by operation.

PRIOR ART

The term an artificial replacement of the hip joint means mostly a metallic implant and partly a non metallic implant. The replacement of a deformed hip joint by an adequate implant, constructed from special stainless biocompatible steel, cobalt or titanium alloy and nonmetallic materials is the most effective mode of eradicating the deformity or destruction of the hip joint and simultaneously a medicotechnical problem, which has been actual practically since 1923 until now and has not been solved satisfactorily by any prevention (Smith-Petersen, M. V.: Evolution of mold arthroplasty of the hip. J. Bone Joint.Surg.1949, 30B:59–75).

Up to now there have been known several constructions of implants for replacement of deformities or destruction of the hip joint, but each of them have, apart from certain advantages, also disadvantages. The well known THR's are typically composed of various components: in the acetabulum a metallic implant, inlay of polyethylene or UHMWPE into which interlocks the head of the femoral stem, which has a conical shape implanted with, or without cement in the femur. In dependence from the development in time, various materials have been used for construction of parts of THR. The development has come to stay today on some well defined materials, which have desired utility properties in respect to the hum an organism. These are materials surgical stainless steel, cobalt alloy, titanium alloy, ultra high molecular weight polyethylene, corundum, zirconium ceramics, a layer of metal applied by plasma spray, a metal grid or hydroxylapatite sprayed on the femoral component of the implant, and an inherent part of the material is surgical methylmethacrylate; with or without hydroxylapatite, which is called bone cement in orthopaedics. The mentioned materials have valuable properties with high strength characteristics, low fatigue limits, abrasive resistance and are biocompatible.

The whole entity of known solutions can be divided into 4 basic groups, which can be characterised as follows.

The First Group of THR.

The first group can be characterised as cemented THR (Charnley J. Low friction arthoplasty of the hip. New York: Springer Verlag, 1970). The basic feature of cemented systems is that the THR is composed of the above mentioned parts; the acetabulum and femoral component (stem) being implanted into the place of the original, but non functional hip joint, where they are fixed by bone cement. These two parts are connected to the femoral head manufactured from metal or ceramics and so finishing a new, functional hip joint. From the functional point of view reconstruction of the original abilities of the hip joint occurs and the patient can walk after some time without external support such as canes, crutches etc.

The Second Group of THR.

This group is represented by systems, which could be characterised as cementless THR (Lintner F., Zweymüller K., Brand G.: Tissue reaction of surrounding to the cementless Ti-6Al-4V after implantation of 7 years. Arch. Orthop Trauma Surg 1988; 1107; 357–366).These are systems with a higher technical and medical effect. Characteristic for this system is its construction from at least two parts, which together create the THR and which is implanted replacing the original-natural, but nonfunctional hip joint. The mentioned components are implanted without cement; the metallic acetabulum is permanently fixed as a "self-drilling" screw or by help of typically three or more screws and the femoral stem, optionally sprayed with a biolayer is implanted into the femur. The special biolayer on the femoral stem is created e.g. by plasma spray of metals or hydroxylapatite, or by special techniques from other materials. Such implants belong to the systems, which totally renew the function of the hip joint.

At present it is possible to mention including both groups of THR world—wide known firms manufacturing and selling THR's: JOHNSON & JOHNSON (USA), ALLOPRO a Company of SULZER MEDICA (Switzerland), WALDEMAR LINK GmbH & Co (Germany), BIOMET LTD and HOWMEDICA LTD (England), BEZNOSKA s.r.o.(Czech Republic), PROTETIM (Hungary), FEHLING-SEFIDAT (Germany) a.o.

The Third Group of THR.

This group is represented by individual, custom made THR (cementless), which are specially constructed after CT scans of the hip and femur of the patient (Aldinger's THR by the firm FEHLING, Individual THR HOWMEDICA). These THR's present the top present state of the art in technics and scientific research in the field of implants; however, the price of these THR's is very high.

The Fourth Group of THR.

This group is comprised of hybrid THR, containing 2–3 parts, where the acetabular part is mostly fixed by screws or special attachments without cement, or is inserted pressfit and the femoral component is cemented (Fehling-Sefidat).

The THR's of all four groups can be constructed by unconventional constructing technologies of chip machining or precision casting, or by pressing technologies of metals and plastics using powder technologies and special technologies for creating a spherical head with unevenly of the surface less than 3 to 4 $\mu$m.

Several known THR's have the disadvantage of not being safe against rotation in the transversal plain or against protrusion in vertical direction. Based on scientific research also the application of cement has the disadvantage of possible thermal injury to the living biomaterial during hardening. Often there is a deficiency in securing a homogenous layer of cement around the implant in the femur by classical cementing methods. In connection with preparing the layer of hydroxylapatite there are difficulties in binding of this layer to the metallic surface and in achieving a homogenous thin layer upon the whole functional surface. The greatest disadvantage of the hydroxylapatite layer is the danger of releasing small particles of hydroxylapatite from the surface of the implant, which can lead to abrasion of the polyethylene part or loosening the femoral stem from the femur. It has also been proven that while hydroxylapatite has a good bony ingrowth, by itself it creates an isolation layer with a high electrical and thermal resistance, blocking a fluent passage of biocurrents in that part of the human skeleton, causing subjective and objective difficulties for the bearer of such an implant.

The aim of the present invention is to offer for medical practice such a THR, which eliminates totally or at least in substantial part the mentioned disadvantages.

SUMMARY OF THE INVENTION

A cementless total replacement of the human hip joint consists typically of 3 or 4 parts, from which the acetabular component is constructed with a self-drilling thread on its surface and after application is fixed to the pelvis. The femoral component (wedge) with at least one rib and at least one groove is fixed into the femur. Both parts are connected by a head with spherical surface which isn't subject of the invention and optionally a polyethylene inlay in the acetabulum, which also isn't subject of the invention.

The substance of the solution resides in the fact that the self-drilling thread is comprised from at least three independent teeth, whereas the outer surface of the mold has advantageously the form of cut spherical or ellipsoid object. The femoral component has in its lower and middle parts a substantially linear inner side and on the outer side or the bottom there is an asymmetrical tapering under the angle γ from the interval of 20 to 70° in relation to the axis of the wedge, which ends in a rounded peak of the wedge. In its middle part the femoral component has a trapezoid shape with a wider upper base, which is connected continuously to the upper part containing a convex broadening on the outer side and traverses continuously to the head. Minimally on the lower and middle parts of the inner side of the femoral component there is provided at least one longitudinal groove, the length and depth of which is at least 0.5 mm, and on at least one side surface of the middle and/or upper part of the femoral component there is at least one rib, defining with the axis of the wedge an angle β in the interval of 70–110° the height and width of which is at least 1 mm.

From the viewpoint of implanting the femoral component into the bone it is advantageous if at least on one side surface of the femoral component there is provided at least one longitudinal rib, parallel to the main axis of the wedge.

Advantageous is further, that at least one tooth has a concave shape of the cutting edge, which ensures a good impact into the pelvic bone with only a minimal defect in the bone. The bony particles during cutting are deposited under the sharp edge of the knife and between the teeth and threads of the self-drilling screw. It is also advantageous, if at least one tooth has a blunt edge which relates mainly to the teeth on the beginning of the self-drilling thread, which minimizes the possibility of damaging soft tissues and vessels. From the viewpoint of minimalizing the damage of tissues is even more advantageous, if the edges of the teeth with either sharp or blunt edges are well rounded. It is also advantageous in this connection if the upper edges of the teeth of the self-drilling thread of the mold (acetabulum) are ground in such a manner that their surfaces lie on a spherical or sphere-like surface, corresponding in shape and dimension to the human acetabulum, which greatly diminishes the danger of cutting the teeth through the pelvic bone and so also the danger of later damage of vessels and nerves in the vicinity of the bone.

To ensure an optimal process of the fixation of the mold (acetabulum), the layer of diamond or hydroxylapatite on at least a part of its outer surface is very advantageous. It is also advantageous if at least on the outer part of the femoral component there is a diamond and/or hydroxylapatite layer. In both above mentioned cases is best, if the diamond layer is in the form of a nanocrystalline layer. The creation of a nanocrystalline diamond or hydroxylapatite layer on the outer surface of the acetabulum or femoral component ensures a better ongrowth and ingrowth of bone on the surface, which is a very important property for the bioprocess in the human body. Above all the layer of nanocrystalline diamond is thermally and electrically conductive and has a very good bony ingrowth, whereas from the physical viewpoint it is in good consent with the biomaterial. A further very important advantage of such a layer is its homogeneity within the whole volume. In consequence of its chemical nature, that means it is a form of carbon in the shape of nanocrystalline diamond, which introduces very good properties in connection with the interaction implant—biomaterial. Its thickness can be regulated by a program and is typically in the range of several nanometers, approximately 3–5 nm. An important property of the layer is, also that it makes a strong chemical bond with the metal surface of the wedge.

The substitution of the human hip joint according to the offered solution has, apart from until now described advantages against solutions of the prior art, a fundamental advantage in its preferable biomechanical properties for the patient, higher fatigue and loosening resistances, whereas the femoral component can be constructed with individual dimensions according to the measurement of the upper part of the femur by adequate medical investigations, while maintaining all the described characteristics.

BRIEF DESCRIPTION OF DRAWINGS

For a better understanding of the invention, the solution is depicted on the enclosed drawings, which are.

DESCRIPTION OF THE PREFERRED EMBODIMENTS

EXAMPLE 1

Figure 1:
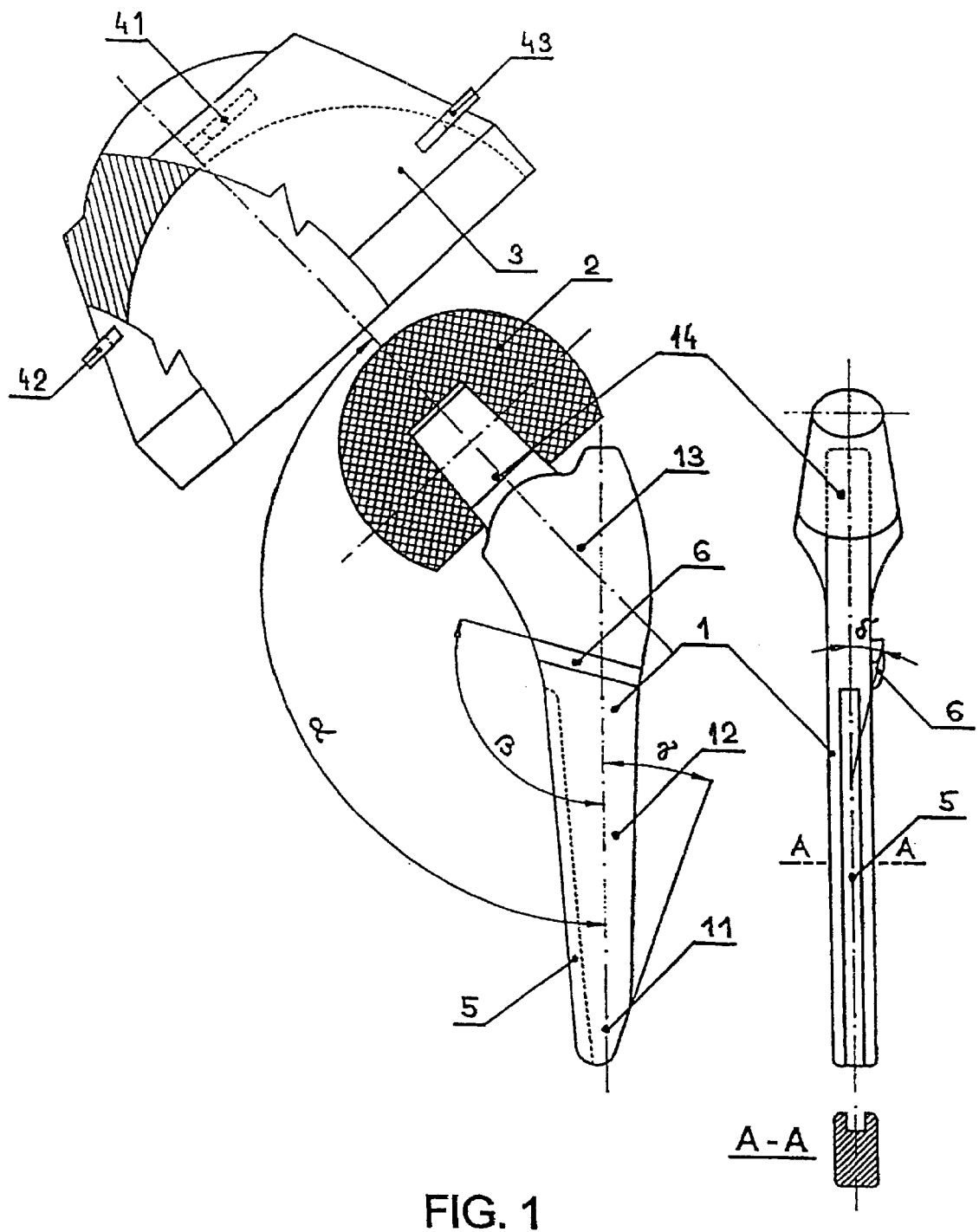
FIG. 1: A global view on the construction of the total replacement of the human hip joint.

Parts of a cementless THR, which are the femoral component 1 and acetabulum 3 (see FIG. 1) constructed from titanium alloy Ti-6Al-4V ELI. The femoral component 1 consists of the lower part 11, middle part 12 and upper part 13 of the main body in the form of a wedge, which ends in its upper part with a cone 14 designated $d_1/d_2 \times L = 12/14 \times 15$ mm. The axis of the cone 14 forms with the main axis of the wedge an angle $\alpha = 132°$, which can be individually adapted to the condition of the patient. The wedge is constructed in such manner that on one main surface is one 3 mm high and 2 mm wide transversal rib 6, which forms with the main axis of the wedge angle β=105°, with which the latter is fixed to the femur. On the inner side of the wedge, i.e. on that side of the femoral component 1, which is turned to the head 2, is on the side surface of the lower part 11 and middle part 12 of the femoral component 1 a longitudinal groove 5 3.0 mm wide. The acetabulum 3, the shape of which is in detail depicted in FIG. 5, has on the cone plane three teeth 41, 42 and 43, the first of which has a truncated pike (shape according to FIG. 7e) and the further two teeth 42, 43 are sharp, i.e. have no truncated pike (see FIG. 7a) and are constructed in a screwline with an angle interval 120° and serve for fixing in the pelvis, on the cone 14 of the femoral component 1 there is the head 2, constructed of corundum, which leans on the spherical plane of the acetabulum 3, thus forming one entity—joint, representing a functional replacement of the human hip joint.

EXAMPLE 2

Figure 2:
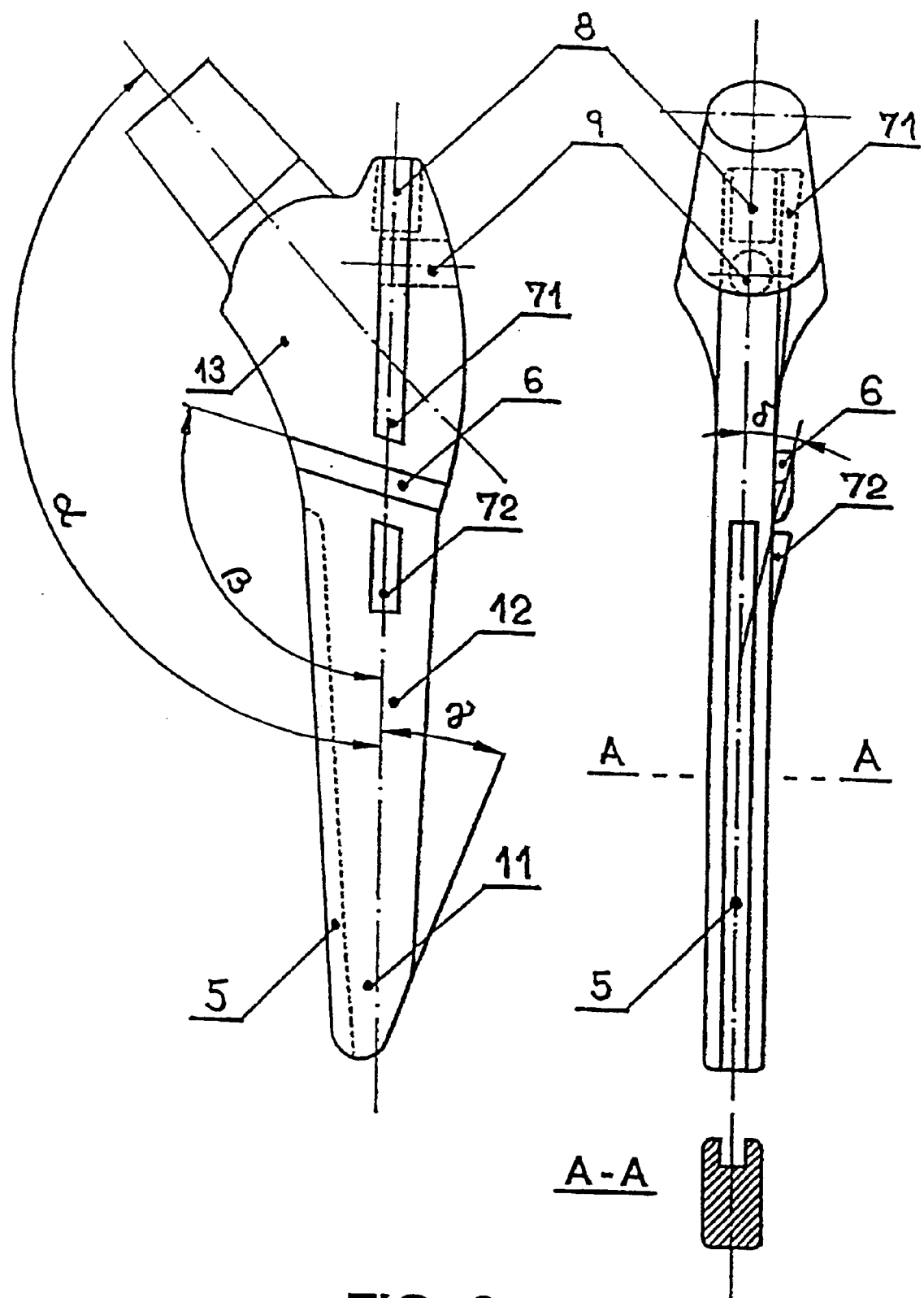
FIG. 2: Femoral component with one transversal rib and two longitudinal ribs on one main surface and one groove on side surface of the wedge.

A total replacement of the human hip joint contains the acetabulum 3, which is constructed from stainless steel according to ISO 5832/211 whereas its shape is basically the same as in example 1 with the difference, that on its outer conical surface, which is covered with a nanocrystalline diamond layer 2 –4 nm thick, there are twelve self-drilling teeth arranged in a screwline in an angular spacing of 90°. The first four teeth in the screwline (in the direction from the top of the acetabulum 3) have truncated pikes, the shape of the teeth corresponding to the embodiment in FIG. 7c, i.e. their cutting edge has a concave shape, but the 5th–12th tooth on the thread have a straight cutting edge and are sharp, i.e. have no truncated pikes (see FIG. 7a). The femoral component 1 (see FIG. 2), which is constructed from a titanium alloy of the type Ti-6Al-4V ELI contains on one main plain one 3 mm high and 3 mm wide transversal rib 6, which forms with the main axis of the wedge an angle β=102° and two 2 mm high and 4 mm wide longitudinal ribs 71, 72, which are parallel with the main axis of the wedge. On the inner side of the wedge there is, on the neighbouring plain on its lower part 11 and middle part 12, a 2.0 mm wide groove. The upper part 13 of the wedge ends in the head 2, which is an integral part of the femoral component 1.

EXAMPLE 3

Figure 3:
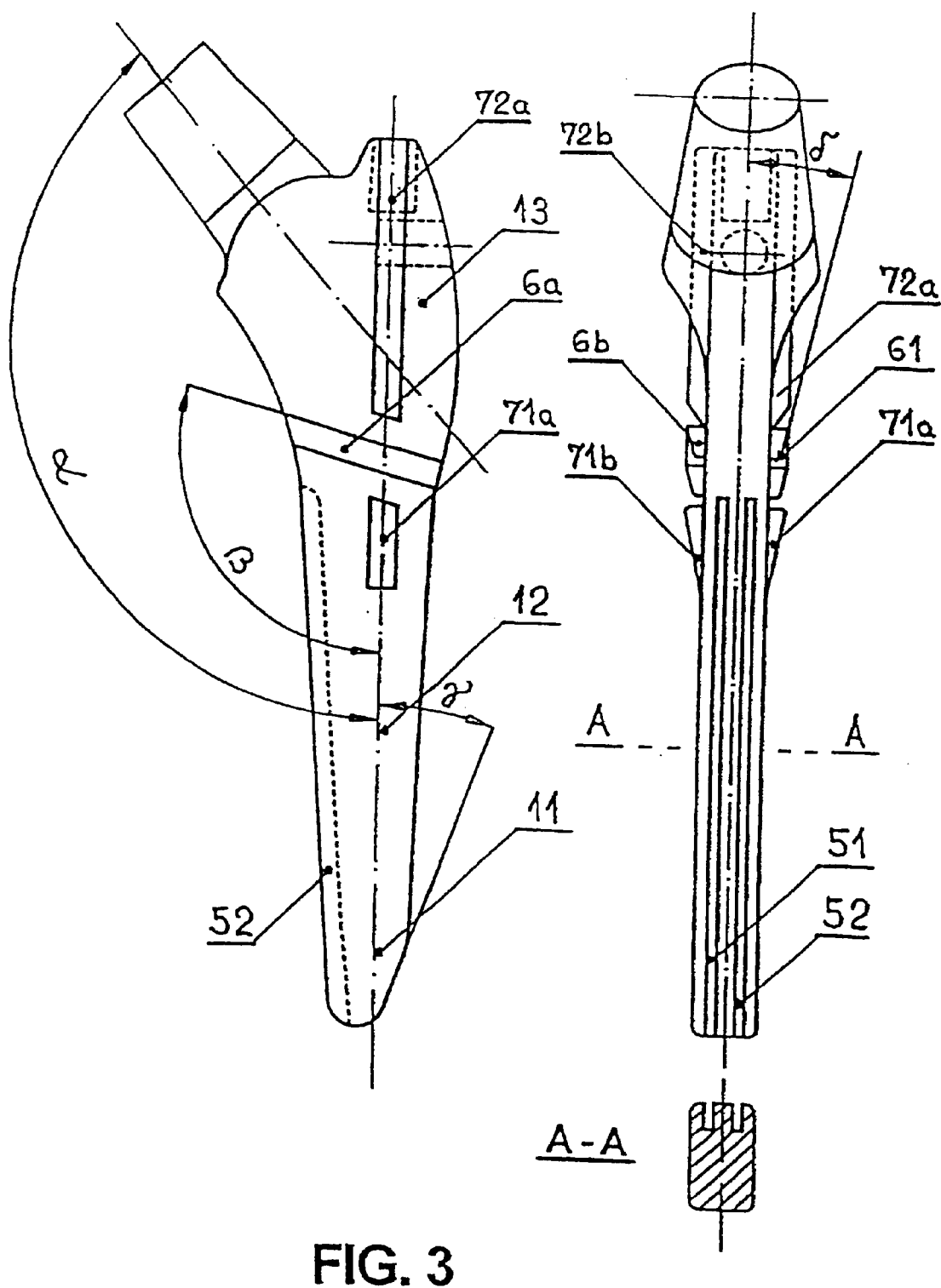
FIG. 3: Femoral component with one transversal rib and two longitudinal ribs on both main surfaces with two parallel grooves on the side surface of the wedge.

The THR of the human hip joint contains an acetabulum 3 according to example 1 with the difference that all three teeth 41, 42 and 43 are sharp (shape according to FIG. 7a) and the femoral component 1 (see FIG. 3), which is constructed from stainless steel according to norm ISO 5832/211 and contains transversal ribs 6a, 6b, each 2 mm high and 2 mm wide, constructed on each main plain and two 3 mm high and 4 mm wide longitudinal ribs 71a, 72a, 71b, 72b made on each main plane and two grooves 51 52 on the side plane in the lower part 11 and middle part 12 of the wedge 1.6 mm wide. The lower part 11, middle part 12 and the upper part 13 of the wedge are covered with a 5–8 μm hydroxylapatite layer.

EXAMPLE 4

Figure 4:
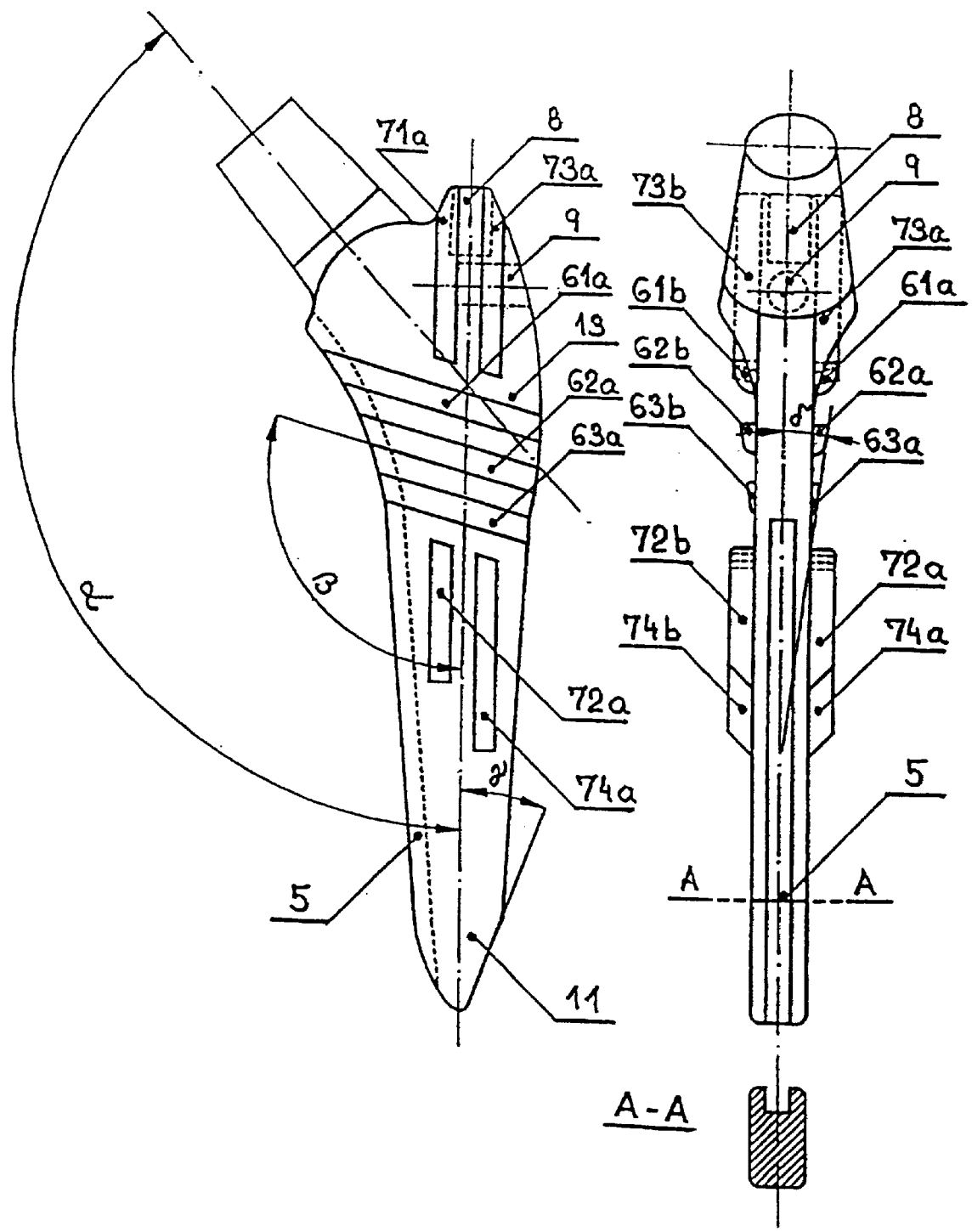
FIG. 4: Femoral component with three transversal ribs and four longitudinal ribs on both main surfaces and one groove on the side surface of the wedge.
Figure 5:
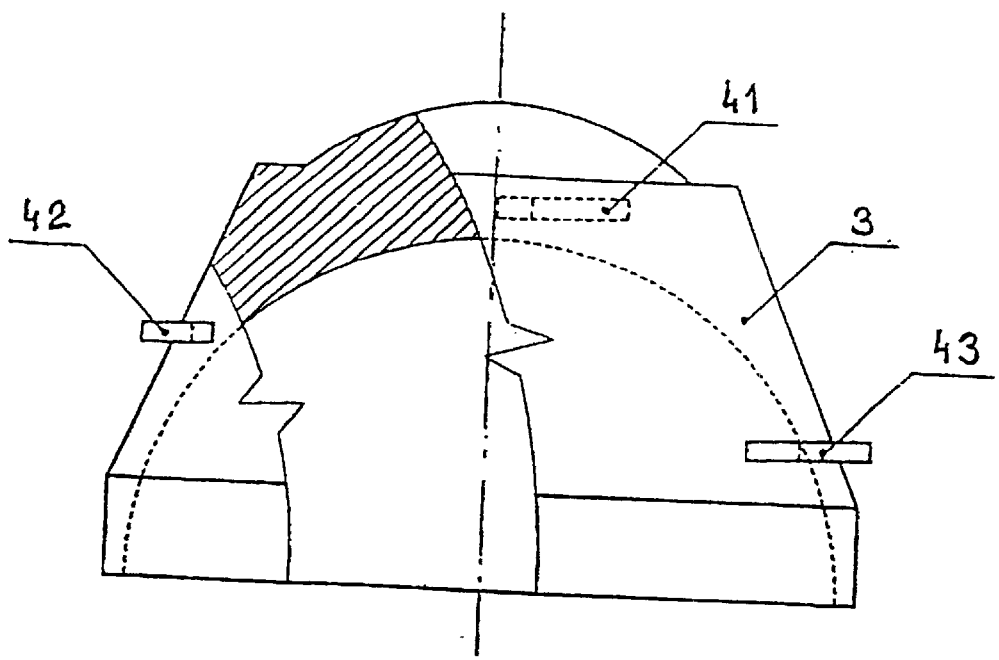
FIG. 5: The mold (acetabulum) with three self-drilling teeth located on the thread with an interval of 120°.
Figure 5:
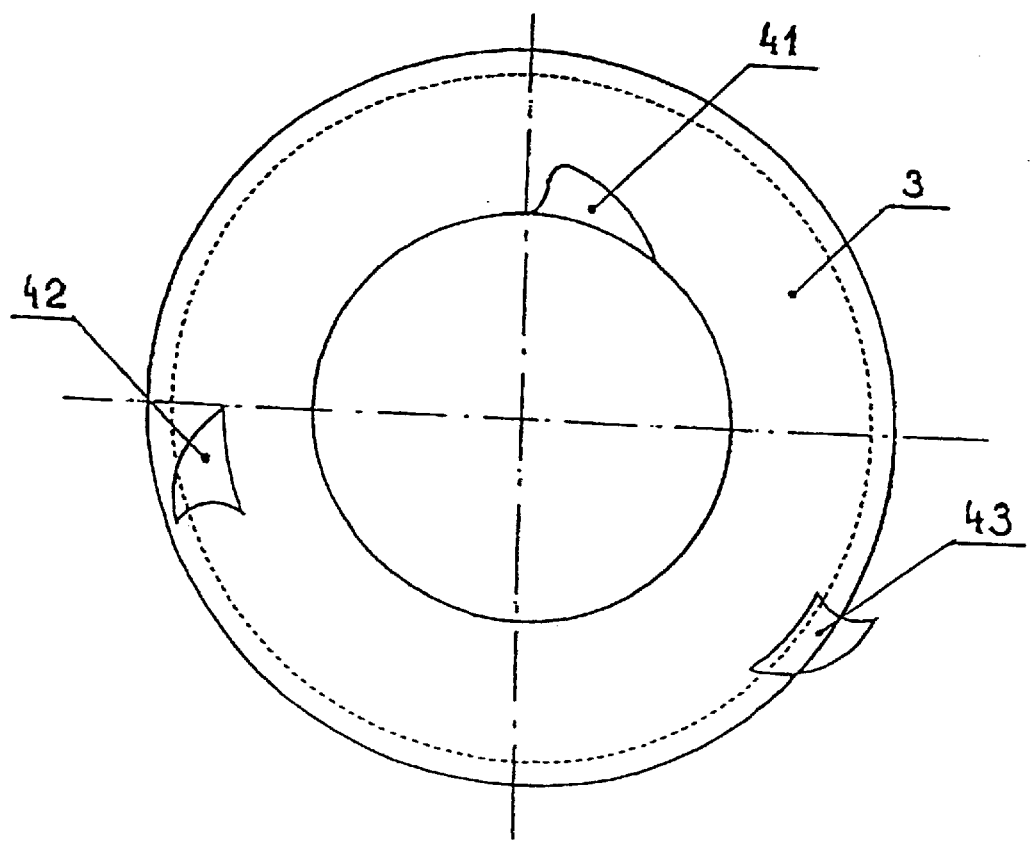

The total replacement of the human hip joint contains the acetabulum 3, according to FIG. 5, the outer surface of which including the self-drilling teeth 41, 42 and 43 are covered by a 3–5 μm thick layer of hydroxylapatite and the femoral component 1 (see FIG. 4), which is constructed from stainless steel according to ISO 5832/211. The femoral component 1 contains the main body in the conical form ended in a standard cone, the axis of which forms with the main axis of the wedge an angle α=120°. The wedge has on each main plain four 3 mm high and 3 mm wide longitudinal ribs 71a, 72a, 73a, 74a, 71b, 72b, 73b and 74b and three 2.5 mm high and 1.5 mm wide transversal ribs 61a, 62a, 63a, 61b, 62b and 63b which form with the main axis of the wedge an angle β=100°. All longitudinal ribs 71a, 72a, 73a, 74a, 71b, 72b, 73b and 74b have on the bottom end a tapering under the angle 45°. The transversal ribs 61a, 62a, 63a, 61b, 62b and 63b are constructed in conical shape with a declination to the main axis of the wedge under the angle δ=5–8° and have a graduated trapezoid cross-section, whereas the join of the longer arm with the shorter arm of the trapezium is made of the radii $r_1$=1.5 mm, $r_2$=1.75 mm and $r_3$=2.0 mm. On the inner side of the wedge there is on its whole length a groove 2.5 mm wide. On the upper part 13 of the wedge is the i.e. introductory opening 8 with sizes d×L=5×8 mm and the i.e. demounting opening 9 with a cross-section of 5 mm and sizes 5×8 mm. The inlay (not depicted) has the shape of a half ball with main sizes of the radii $R_1$=14 mm and $R_2$=25 mm, which has on its lower part two or more piston pivots with sizes d×L=5×1.0 mm and is inserted into the acetabulum with an overlap.

EXAMPLE 5

Figure 6:
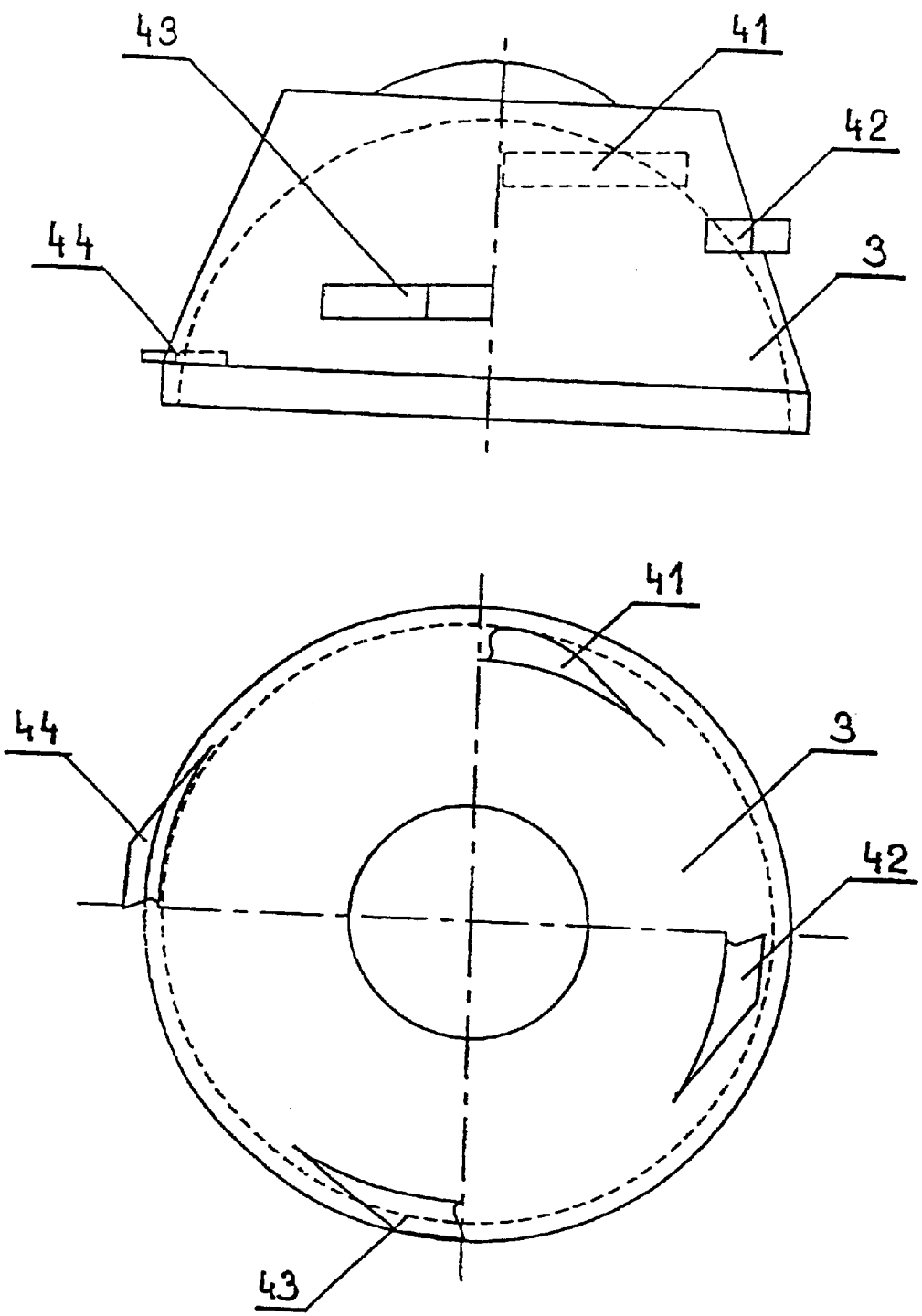
FIG. 6: Acetabulum with four self-drilling teeth located on the thread with an interval of 90°.
Figure 7:
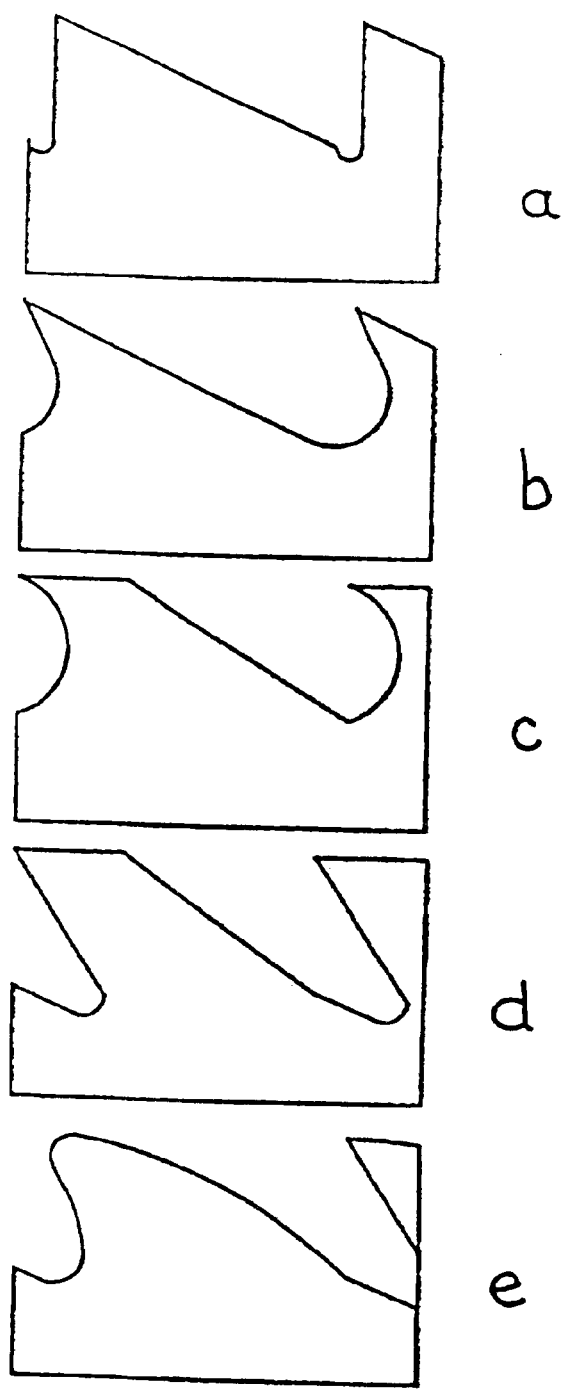
FIG. 7: Schematic depicting of advantageous forms of self-drilling teeth:
 a) tooth with a vertical cutting edge and sharp pike
 b) tooth with a concave cutting edge and sharp pike
 c) tooth with concave cutting edge and truncated pike
 d) tooth with a sharpened cutting edge and truncated pike
 e) tooth with a sharpened cutting edge and truncated and well rounded pike in the form of a spiral of Archimedes or logarithmic screwline.

Total replacement of the human hip joint according to example 1 having the difference that the acetabulum 3 has a shape according to FIG. 6, i.e. on its conical surface there are in an angular spacing of 90° four teeth 41, 42, 43 and 44, wherein the first tooth 41 has a shape according to FIG. 7e and the other three teeth 42, 43 and 44 have a shape according to FIG. 7d. Apart from this the head 2 in compound state leans on the inner spherical plane of the non represented inlay (this is not part of the solution) constructed of high molecular polyethylene and only the latter with its outer spherical plane leans on the inner plane of the acetabulum 3.

EXAMPLE 6

Figure 8:
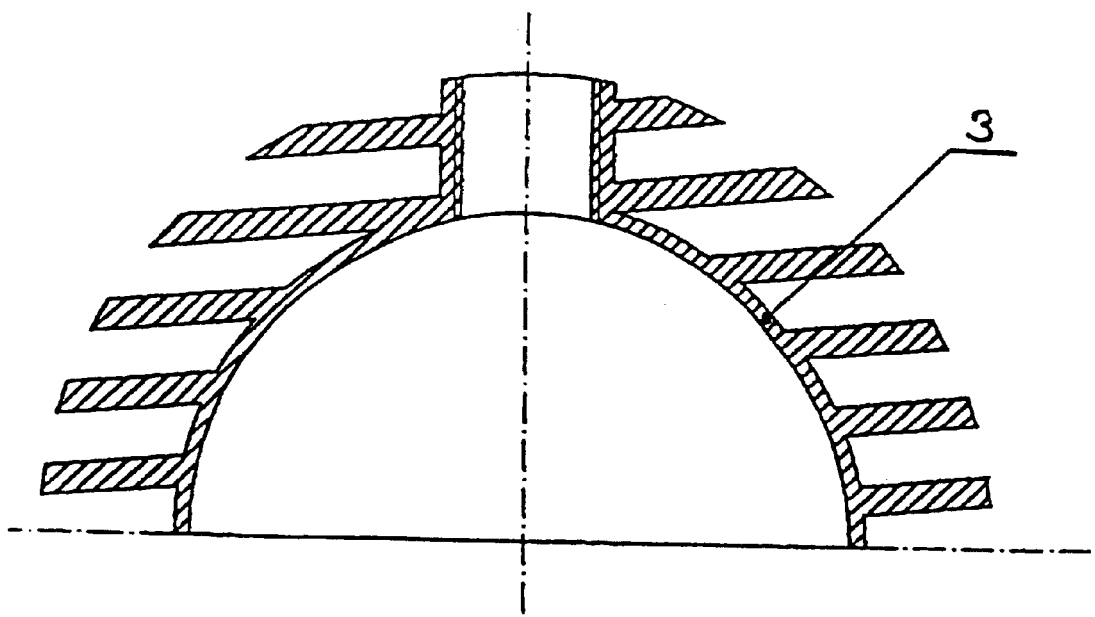
FIG. 8: Schematic depiction of the acetabulum with several self-drilling teeth constructed so that their upper edges are hemispherical.

Total replacement of the human hip joint according to example 2 having the difference that the acetabulum 3 has its outer surface of the shape of a half ball (see FIG. 8) on the pole of which there is an opening with a thread. The self-drilling thread consists of twenty four teeth, which are located in a screwline with an ascent 5° in an angular spacing of 90°. Further, all teeth have truncated and rounded pikes and a shape according to FIG. 7e, wherein the outer parts of the teeth are constructed in such a manner that they are on the spherical surface. On the surface of the acetabulum 3 and the teeth there is a hydroxylapatite layer 4–7 μm thick.

EXAMPLE 7

Total replacement of the human hip joint according to example 6 having the difference that the acetabulum 3 contains altogether twelve self-drilling teeth, located in a screwline in three threads with an angular spacing of 90°, wherein the teeth in the first thread have cut-down cutting surface and cut-down pike. (see FIG. 7d). The teeth in the second and third thread have a concave shape of the cutting edge and a cut-down in the form of a logarithmic thread (see FIG. 7e). On the surface of the acetabulum 3 and teeth a 3–4 nm thick nanocrystalline diamond layer is constructed.

EXAMPLE 8

Total replacement of the human hip joint according to example 6 difference that the self-drilling thread consists of forty eight teeth, which are located on the large thread with an ascension 5° in an angular spacing of 30°.

Industrial Applicability

The solution of the invention can be according to its properties succesfully applied to the majority of all until now known deformities, destruction and traumatic lesions of the hip joint.

What is claimed is:

1. A cementless total replacement of the human hip joint comprising an acetabulum, on the outer surface of which there is provided a self-drilling thread, a head, and a femoral component in the shape of a flat wedge, wherein the self-drilling thread comprises at least three independent teeth, the femoral component has an inner side, a lower part and a middle part and a substantially linear inner side in its lower and middle parts, and an asymmetrical tapering on the outer side of its lower part under an angle γ equal to 20° to 70° in respect to the axis of the wedge, which ends in the pike of the wedge, and wherein that in the middle part, the femoral component has a trapezoidal shape with a wider upper basis continuously tied with the upper part which contains a convexly widened outer side and ends in a transitional part to the head, wherein there is provided at least on the lower part and on the middle part of the inner side of the femoral component at least one longitudinal groove, the width and depth of which are at least 0.5 mm each, and there is provided on at least one side surface of at least one of the middle part and the upper part of the femoral component at least one transversal rib having each of the height and width 1 mm minimum, which forms an angle β equal to 70° to 110° with the axis of the wedge.

2. A cementless total replacement as set forth in claim 1 wherein at least one tooth of the self-drilling thread has a concave shape of the cutting edge.

3. A cementless total replacement as set forth in claim 2 wherein the wedge has a main axis and at least on one side surface of the femoral component there is provided at least one longitudinal rib parallel with the main axis of the wedge.

4. A cementless total replacement as set forth in claim 2 wherein the upper edges of the teeth of the self-drilling thread of the acetabulum lie on a substantially spherical surface.

5. A cementless total replacement as set forth in claim 1 wherein at least one tooth of the self-drilling thread has a truncated pike.

6. A cementless total replacement as set forth in claim 5 wherein the wedge has a main axis and at least on one side surface of the femoral component there is provided at least one longitudinal rib parallel with the main axis of the wedge.

7. A cementless total replacement as set forth in claim 5 wherein the upper edges of the teeth of the self-drilling thread of the acetabulum lie on a substantially spherical surface.

8. A cementless total replacement as set forth in claim 1 wherein the acetabulum has an outer surface and at least on a part of the outer surface of the acetabulum there is provided a layer of one of the group consisting of diamond and hydroxyapatite.

9. A cementless total replacement as set forth in claim 8 wherein the layer is a diamond layer which is a nanocrystalline diamond layer.

10. A cementless total replacement as set forth in claim 8, wherein the femoral component has an outer surface and at least on a part of the outer surface of the femoral component there is provided a layer of one of the group consisting of diamond and hydroxyapatite.

11. A cementless total replacement as set forth in claim 8 wherein the wedge has a main axis and at least on one side surface of the femoral component there is provided at least one longitudinal rib parallel with the main axis of the wedge.

12. A cementless total replacement as set forth in claim 8 wherein the upper edges of the teeth to the self-drilling thread of the acetabulum lie on a substantially spherical surface.

13. A cementless total replacement as set forth in claim 1 wherein the femoral component has an outer surface and at least on a part of the outer surface of the femoral component there is provided a layer of one of the group consisting of diamond and hydroxylapatite.

14. A cementless total replacement as set forth in claim 13, wherein the layer is a diamond layer which is a nanocrystalline diamond layer.

15. A cementless total replacement as set forth in claim 13 wherein the wedge has a main axis and at least on one side surface of the femoral component there is provided at least one longitudinal rib parallel with the main axis of the wedge.

16. A cementless total replacement as set forth in claim 1 wherein the wedge has a main axis and at least on one side surface of the femoral component there is provided at least one longitudinal rib parallel with the main axis of the wedge.

17. A cementless total replacement as set forth in claim 16 wherein the upper edges of the teeth of the self-drilling thread of the acetabulum lie on a substantially spherical surface.

18. A cementless total replacement as set forth in claim 1 wherein the upper edges of the teeth of the self-drilling thread of the acetabulum lie on a substantially spherical surface.

19. A cementless total replacement as set forth in claim 1, including an inlay positioned between the head of the femoral component and the acetabulum.

20. A cementless total replacement as set forth in claim 1, wherein the at least one tooth of the self-drilling thread has a rounded pike.

* * * * *